United States Patent
Good et al.

(10) Patent No.: US 9,539,316 B2
(45) Date of Patent: Jan. 10, 2017

(54) BLOOD STAGE MALARIA VACCINE

(75) Inventors: Michael Good, Queensland (AU); Terry W. Spithill, Bundoora (AU); Moses Lee, Holland, MI (US)

(73) Assignees: Griffth University, Nathan, Queensland (AU); La Trobe University, Bundoora, Victoria (AU)

( * ) Notice: Subject to any disclaimer, the term of this patent is extended or adjusted under 35 U.S.C. 154(b) by 33 days.

(21) Appl. No.: 14/122,701

(22) PCT Filed: May 28, 2012

(86) PCT No.: PCT/AU2012/000594
§ 371 (c)(1),
(2), (4) Date: Mar. 14, 2014

(87) PCT Pub. No.: WO2012/162731
PCT Pub. Date: Dec. 6, 2012

(65) Prior Publication Data
US 2014/0186402 A1    Jul. 3, 2014

Related U.S. Application Data

(60) Provisional application No. 61/617,435, filed on Mar. 29, 2012, provisional application No. 61/490,761, filed on May 27, 2011.

(30) Foreign Application Priority Data

Aug. 23, 2011 (NL) ..................................... 2007292

(51) Int. Cl.
*A61K 39/00* (2006.01)
*A61K 39/015* (2006.01)
*C07K 14/445* (2006.01)

(52) U.S. Cl.
CPC ........... *A61K 39/015* (2013.01); *C07K 14/445* (2013.01); *A61K 2039/522* (2013.01)

(58) Field of Classification Search
CPC .................................................. A61K 39/015
See application file for complete search history.

(56) References Cited

U.S. PATENT DOCUMENTS

2005/0208078 A1 * 9/2005 Hoffman et al. .......... 424/272.1

FOREIGN PATENT DOCUMENTS

WO    2008/050140    5/2008

OTHER PUBLICATIONS

Plotkin (Vaccines W. B. Saunders Company, 1988, p. 571).*
Chavda, S., et al. "A novel achiral seco-cyclopropylpyrido[e]indolone (CPyI) analog of CC-1065 and the duocarmycins: synthesis, DNA interactions, in vivo anticancer and anti-parasitic evaluation." Bioorg Med Chem. Jul. 15, 2010;18(14):5016-24. Epub Jun. 4, 2010.
Lee, M., et al. "ORGN 5-Centanamycin: a powerful and new antimalarial agent that targets the minor groove of the A/T rich plasmodium genome" American Chemical Society Papers Abstracts. Feb. 11, 2008;235.
Purcell, L.A., et al. "Chemically attenuated Plasmodium sporozoites induce specific immune responses, sterile immunity and cross-protection against heterologous challenge." Vaccine. Sep. 8, 2008;28(38):4880-4. Epub Jul. 29, 2008.
Purcell, L.A., et al. "Chemical attenuation of Plasmodium berghei sporozoites induces sterile immunity in mice." Infect Immun. Mar. 2008;76(3):1193-9. Epub Jan. 3, 2008.
Yanow, S.K., et al. "Potent antimalarial and transmission-blocking activities of centanamycin, a novel DNA-binding agent." J Infect Dis. Feb. 15, 2008;197(4):527-34.

* cited by examiner

*Primary Examiner* — Albert Navarro
*Assistant Examiner* — Mark Navarro
(74) *Attorney, Agent, or Firm* — Kathleen D. Rigaut; Dann, Dorfman, Herrell & Skillman

(57) ABSTRACT

An immunogenic composition for use as a blood-stage malaria vaccine, a method of producing the immunogenic composition and a method of treatment of malaria are provided. The immunogenic composition includes isolated or purified merozoites, or red blood cells infected with merozoites, treated with centanamycin or tafuramycin A. The immunogenic composition does not include an adjuvant. A single dose of the immunogenic composition is sufficient to protect an animal against subsequent malaria infection by the same isolate, strain or species of *Plasmodium* used in the immunogenic composition, or by one or more heterologous isolates, strains or species of *Plasmodium*.

18 Claims, 8 Drawing Sheets

BLOOD STAGE MALARIA VACCINE

The present application is §371 application of PCT/AU2012/00594 filed May 28, 2012 which claims priority to NL Patent Application No. 2007292 filed Aug. 23, 2011, U.S. Provisional Application No. 61/617,435 filed Mar. 29, 2012, and 61/490,761 filed May 27, 2011, the entire disclosure of each being incorporated by reference herein.

TECHNICAL FIELD

THIS INVENTION relates to malaria. More particularly, this invention relates to the use of chemically-attenuated malaria merozoites as a vaccine against blood-stage malaria.

BACKGROUND

An effective malaria vaccine will represent a cost-effective and sustainable addition to the currently available malaria control interventions. Malaria vaccines have attempted to target the different stages of malaria infection, typically referred to as the "sporozoite stage", the "liver stage" and "blood-stage". The liver stage occurs when sporozoites infect host hepatocytes, multiplying asexually and asymptomatically for a period of 8-30 days. Once in the liver, these organisms differentiate to yield thousands of merozoites which, following rupture of their host cells, escape into the blood and infect red blood cells, thus beginning the erythrocytic or "blood-stage" of the life cycle. Within the red blood cells, the parasites multiply further, again asexually, periodically breaking out of their hosts to invade fresh red blood cells. Several such amplification cycles occur. Thus, classical descriptions of waves of fever arise from simultaneous waves of merozoites escaping and infecting red blood cells.

Anti-asexual blood-stage vaccines have been aimed at reducing parasite growth and multiplication in the blood and, hence, the occurrence or severity of symptoms. Such vaccines should reduce morbidity and mortality due to malaria, in the most susceptible groups (e.g. young children and pregnant women) living in areas where malaria is endemic.

One approach has been to trial recombinant subunit vaccines against blood-stage malaria, but to date none of the subunit blood-stage vaccine candidates have progressed beyond Phase III trials.

An alternative approach has been to use whole blood-stage parasites (e.g. merozoites). Whole blood-stage parasites were first administered to monkeys in 1948 when Freund attempted to develop a whole parasite vaccine. Over the following 30 years there were in excess of 12 separate studies in monkeys (summarized in McCarthy and Good, 2010) until malaria antigens were first cloned in 1983, which ushered in the subunit paradigm era. The whole parasite strategy was abandoned for blood-stage vaccine development because very large numbers of parasites were thought to be required ($5 \times 10^7$-$10^{10}$), making it impossible to prepare such a vaccine at scale in human blood. The only adjuvant shown to be useful was the human-incompatible complete Freund's adjuvant.

More recently, a "low-dose whole parasite" approach has been attempted which may be characterized as follows: (i) it aims to induce a cellular (T cell) immune response, as opposed to an antibody response; (ii) very low doses of parasites are not only sufficient but essential to keep doses low; and (iii) heterologous immunity is induced because presumably the target antigenic determinants of T cells are highly conserved between Plasmodium strains and species (Pinzon-Charry et al, 2010), thereby obviating one of the major impediments of sub-unit vaccines that aim to induce antibodies that target polymorphic merozoite or infected red cell surface proteins. Furthermore, very low doses of parasites overcome the logistic impediment of finding sufficient blood to prepare a vaccine at scale or the need to find a way to grow the parasites in axenic culture. The two critical factors of parasite dose and cellular immune response are in fact closely related. In order to induce a strong cellular immune response it is important to use only a very low dose of parasites (Elliott et al, 2005).

Three studies are reported in which humans or mice have been immunized with ultra low doses of whole parasites—two in which vaccines received an ultra low dose of live infected red cells (with infection terminated by drug early before parasites were visible in the blood by microscopy; Elliott et al, 2005; Pombo et al, 2002), and the other in which mice were immunized with 100-1000 killed infected red cells mixed with CpG and Alum for the primary immunization (Pinzon-Charry et al, 2010). In both humans and mice the immune responses were characterized by a strong in vitro proliferative response to parasites of $CD4^+ +/- CD8^+$ T cells, secretion of γ-interferon and induction of nitric oxide synthase in peripheral blood mononuclear cells. Parasite-specific antibodies were either not induced, or induced at very low levels. Memory T cells (both 'central' and 'effector') were induced. It has been proposed that induced memory T cells will have specificity for internal antigens of the parasite and that these will be highly conserved as they are not under immune selective pressure from B cells and antibody. This has been shown to be the case for the one major T cell target antigen of Plasmodium falciparum identified so far, the purine salvage enzyme, HGXPRT (Makobongo et al, 2003) where immunity appeared to be mediated solely by T cells.

The requirement for purine nucleotide salvage by blood-stage malaria parasites has been exploited by making genetically-attenuated malaria parasites lacking a functional gene encoding the purine nucleotide transporter 1 (Pynt1–), which upon administration to mice provided sterile immunity against subsequent malaria infection (Ahmed et al., 2010; International Publication 2008/094183). However, the applicability of this approach to humans is questionable because of the possibility of selection of genetic "breakout" following administration to humans.

SUMMARY

The present invention recognizes that whole malaria parasite vaccine preparations to date have consisted of either a live infection (followed by drug cure before parasitemia became patent and symptomatic) or a freeze/thaw preparation that required CpG and alum to be effective. Neither of these delivery modalities is suitable for human use. Furthermore, the use of genetically-attenuated whole malaria parasites in humans is hindered by concerns about safety. Surprisingly, treatment of merozoites or red blood cells infected with merozoites, with DNA-binding agents such as tafuramycin A or centanamycin, or analogs or derivatives of these, attenuate the merozoites sufficiently to enable administration of the merozoites or infected red blood cells for the purposes of immunization against malaria. Even more surprisingly, this immunization is effective as a single dose in the absence of adjuvant. A further unexpected benefit is that the treated merozoites of a particular malaria isolate, strain or species of *Plasmodium* will immunize against infection by heterologous *Plasmodium* isolates, strains and species.

The invention is therefore broadly directed to a vaccine composition comprising chemically attenuated whole, blood-stage malaria parasites, preferably in the absence of adjuvant.

A preferred approach includes the administration of a low dose of attenuated blood-stage malaria parasites, either as parasite-infected red blood cells or as purified blood-stage parasites in the absence of adjuvant. Even more preferably, a single low dose of attenuated blood-stage malaria parasites or infected red blood cells is sufficient to immunize against subsequent malaria infection.

Preferably, the parasite-infected red blood cells are intact cells.

In one aspect, the invention provides a method of producing an immunogenic composition including the step of treating blood-stage malaria parasites or red blood cells infected with said blood-stage malaria parasites with centanamycin, tafuramycin A or an analog or derivative thereof, to thereby produce said immunogenic composition.

Suitably, the method excludes the step of including an adjuvant.

In another aspect, the invention provides an immunogenic composition comprising blood-stage malaria parasites or red blood cells infected with said blood-stage malaria parasites that have been treated with centanamycin, tafuramycin A or an analog or derivative thereof; and an immunologically acceptable carrier, diluent or excipient.

Suitably, the immunogenic composition does not include an adjuvant.

In yet another aspect, the invention provides an immunogenic composition for use in treating or preventing malaria, said immunogenic composition comprising blood-stage malaria parasites or red blood cells infected with said blood-stage malaria parasites that have been treated with centanamycin, tafuramycin A or an analog or derivative thereof; and an immunologically acceptable carrier, diluent or excipient.

Suitably, the immunogenic composition does not include an adjuvant.

In a further aspect, the invention provides a method of treating or preventing malaria, said method including the step of administering the immunogenic composition of the aforementioned aspect to an animal to thereby prevent or inhibit malaria infection or treat an existing malaria infection in said animal.

Preferably, the method includes administering a single dose of said immunogenic composition to thereby prevent or inhibit malaria infection or treat an existing malaria infection in said animal.

Suitably, the method does not include administration of an adjuvant.

Typically, the blood-stage malaria parasites or red blood cells infected with said blood-stage malaria parasites are a "low dose" of blood-stage malaria parasites.

Typically, according to the aforementioned aspects the blood-stage malaria parasites include, or are, merozoites, schizonts, rings or trophozoites, although without limitation thereto.

Preferably, the animal of the aforementioned aspects is a human.

Throughout this specification, unless the context requires otherwise, the words "comprise", "comprises" and "comprising" will be understood to imply the inclusion of a stated integer or group of integers but not the exclusion of any other integer or group of integers.

DETAILED DESCRIPTION

Figure 1:
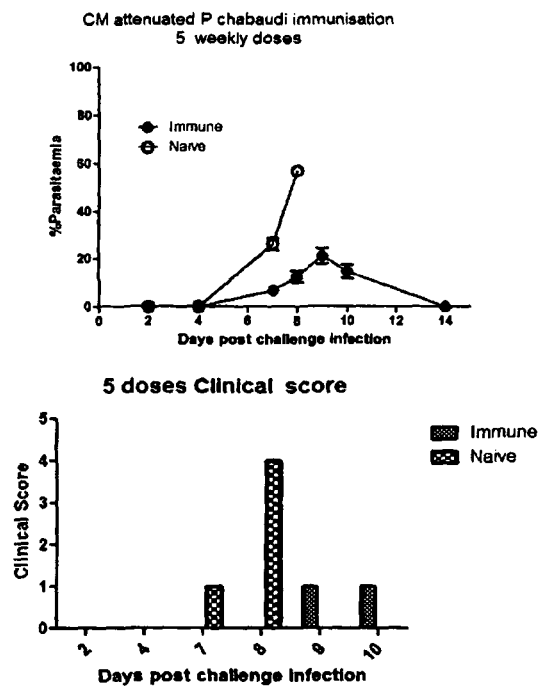
FIG. 1: A/J mice were vaccinated with 5 doses of $10^4$ *P. chabaudi* parasitized RBCs (pRBC). Parasites were attenuated in vitro using centanamycin at 2 µM for 40 minutes. pRBC were then washed extensively before being administered to mice. Mice were challenged with *P. chabaudi* ($10^5$ pRBC/mouse—iv) 21 days after the final vaccination. Data in the upper panel represent mean parasitemia of 5 mice per group +/−SEM. Naïve mice all succumbed or were euthanased by day 8. Data in the lower panel show the clinical scores with 0 representing no signs of any distress.

The present invention is predicated at least partly on the discovery that a single, low dose of centanamycin- or tafuramycin A-treated blood-stage malaria parasites (e.g merozoites, schizonts, rings or trophozoites, although without limitation thereto) or red blood cells infected with same, effectively immunize against subsequent malaria infection in the absence of adjuvant. Furthermore, centanamycin- or tafuramycin A-treated merozoites of a particular malaria isolate, strain or species will immunize against infection by heterologous malaria isolates, strains and species. One particular feature of the invention is that immunization with parasitized red blood cells (pRBC) treated according to the invention is optimal using intact pRBC.

Accordingly, in one preferred aspect, the invention provides a method of producing an immunogenic composition including the step of treating isolated or purified blood-stage malaria parasites or red blood cells infected with said blood-stage malaria parasites with centanamycin, tafuramycin A or an analog or derivative thereof, to thereby produce said immunogenic composition.

In another preferred aspect, the invention provides an immunogenic composition comprising a low dose of isolated or purified blood-stage malaria parasites or red blood cells infected with said blood-stage malaria parasites that have been treated with centanamycin, tafuramycin A or an analog or derivative thereof, said composition excluding adjuvant.

In yet another preferred aspect, the invention provides an immunogenic composition for preventing or treating malaria, said immunogenic composition comprising a low dose of isolated or purified blood-stage malaria parasites or red blood cells infected with said blood-stage malaria parasites that have been treated with centanamycin, tafuramycin A or an analog or derivative thereof, said composition excluding adjuvant.

In a further preferred aspect, the invention provides a method of treating or preventing malaria, said method including the step of administering the immunogenic composition of the aforementioned aspect to an animal to thereby prevent or inhibit malaria infection or treat an existing malaria infection in said animal, said method excluding administration of adjuvant.

Typically, the blood-stage malaria parasites are, or include, merozoites schizonts, rings or trophozoites, although without limitation thereto. For example, the blood-stage malaria parasites may be purified merozoites or a' mixture of isolated merozoites and other blood-stage malaria parasites such as schizonts, rings and/or trophozoites.

It will be appreciated from the foregoing that one embodiment of the invention relates to in vitro treatment of isolated or purified blood-stage malaria parasites such as merozoites or red blood cells infected with blood-stage parasites (e.g. merozoites, schizonts, rings or trophozoites, although without limitation thereto), with centanamycin, tafuramycin A or an analog or derivative of centanamycin or tafuramycin A. This treatment is effective to chemically attenuate the blood-stage malaria parasites (e.g. merozoites, schizonts, rings or trophozoites, although without limitation thereto) without killing the parasite, such as by inhibiting parasite replication. Typically, the attenuated blood-stage malaria parasites are not capable of proliferation, or are capable of only limited proliferation, following attenuation by treatment with centanamycin or tafuramycin A.

Centanamycin is a rationally designed, achiral DNA binding and alkylating agent based on (+)-duocarmycin SA that lacks a stereocenter. Centanamycin binds covalently to adenine-N3 in the DNA sequence motif (A/T)AAA.

Tafuramycin A is a rationally designed, DNA binding and alkylating agent based on duocarmycins that comprises a stereocenter.

By "centanamycin or tafuramycin A analogs or derivatives" is meant any molecule structurally related to centanamycin or, tafuramycin A which exhibits binding to AT-containing nucleotide sequences to thereby induce DNA damage.

Centanamycin, tafuramycin A, analogs or derivatives inclusive of non-chiral, chiral and racemic analogs and derivatives of duocarmycin and CC-1065, non-chiral, chiral and racemic isomers, salts or solvates thereof are also described in WO2002/030894, WO2008/050140, WO2009/064908, Howard et al., 2002 and Purnell et al., 2006, Chavda et al., 2010 and U.S. Pat. No. 6,660,742. Reference is particularly made to seco-iso-cyclopropylfurano[2,3-e]indoline-TMI (TH-III-149 or tafuramycin A) and seco-cyclopropyltetrahydrofurano[2,3-f]quinoline-TMI (TH-III-151 or tafuramycin B) analogs of CC-1065 and the duocarmycins as described in Howard et al., 2002, supra and Purnell et al., 2006, supra.

Achiral seco-hydroxy-aza-CBI-TMI, a seco-cyclopropylpyrido[e]indolone (CPyI) compound, is an example of an analog of centanamcyin as described in Chavda et al., 2010, supra. Racemic and chiral 5-methylfuran analogs of tafuramycin A are described in Purnell et al., 2006, supra.

In a preferred embodiment, centanamycin, tafuramycin A or the analog or derivative is a compound of formula I:

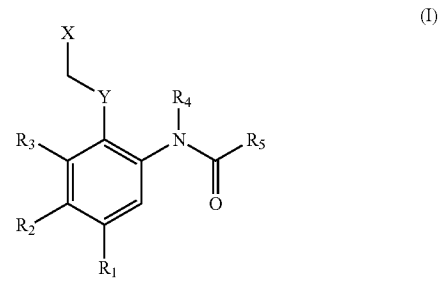

(I)

wherein, $R_1$ is either NHR or OR, where R is selected from H, benzyl, benzyloxycarbonyl, 4-nitrobenzyloxycarbonyl and N'-methylpiperazinyl-N-carbonyl;

$R_2$ is selected from H and $C_{1-6}$ alkyl;

R₃ is selected from H and $C_{1-6}$ alkyl; or R₂ and R₃, form a fused ring selected from the group consisting of a benzene ring, a pyrrole ring, a pyridine ring, a furan ring and a 5-methylfuran ring, which fused ring may be optionally substituted with $C_{1-6}$ alkyl, $CF_3$ or $C_{1-6}$ alkyloxycarbonyl;

Y is an alkylene radical selected from —CH₂—, —CH₂CH₂— or —CH₂CH₂CH₂—; or Y may be —CH— to form a five-membered ring with R₄;

X is an electrophilic leaving group;

R₄ is selected from H, $C_{1-6}$ alkyl, a —CH₂— group bonded to Y to form a five-membered ring or a —CH₂— group bonded to the —CH₂— to which X is attached to form a six membered ring;

R₅ is selected from the group consisting of:

(a)

where Y₁ and Y₂ are independently selected from O and NH;

(b)

(c)

(d)

(e)

where Y₃ is selected from O and NH;

(f)

(g)

(h)

(i) t-butoxy, benzyloxy and 9-fluorenylmethyloxy.

In one particular embodiment of the compound of formula I:

Preferably, R₁ is OH.

Preferably, R₂ and R₃ together form a furan ring.

Preferably, Y is —CH— and forms a five-membered ring with R₄.

Preferably, X is selected from chloro, bromo, iodo, mesylate, tosylate, thio, ammonium, $C_{1-6}$ alkylsulfonyl and $C_{1-6}$ alkylsulfoxyl.

More preferably, X is selected from chloro, bromo, iodo, mesylate and tosylate.

Even more preferably, X is chloro.

Preferably, R₄ is a —CH₂— group bonded to Y to form a five membered ring structure.

Preferably, R₅ is:

A preferred form of this embodiment is a compound of Formula II (tafuramycin A):

(II)

In another embodiment of the compound of Formula I:
Preferably, R₁ is NH₂.
Preferably, R₂ and R₃ together form a benzene ring.
Preferably, Y is —CH—.
Preferably, X is selected from chloro, bromo, iodo, mesylate, tosylate, thio, ammonium, C$_{1-6}$ alkylsulfonyl and C$_{1-6}$ alkylsulfoxyl.
More preferably, X is selected from chloro, bromo, iodo, mesylate and tosylate.
Even more preferably, X is chloro.
Preferably, R₄ is H or C$_{1-6}$ alkyl.
Preferably, R₅ is A preferred form of this embodiment is a compound of Formula III (centanamycin):

(III)

In yet another embodiment of the compound of Formula I:
Preferably, R₁ is OH.
Preferably, R₂ and R₃ together form a pyridine ring optionally substituted with C$_{1-6}$ alkyl.
Preferably, Y is —CH—.
Preferably, X is selected from chloro, bromo, iodo, mesylate, tosylate, thio, ammonium, C$_{1-6}$ alkylsulfonyl and C$_{1-6}$ alkylsulfoxyl.

More preferably, X is selected from chloro, bromo, iodo, mesylate and tosylate.
Even more preferably, X is chloro.
Preferably, R₄ is H or C$_{1-6}$ alkyl.
Preferably, R₅ is A preferred form of this embodiment is a compound of Formula IV (AS-VIII-104):

(IV)

Typical, although non-limiting concentrations of centanamycin, tafuramycin A or analogs or derivatives for treatment of blood-stage malaria parasites are in the range 0.01 to 10 μM. Preferably, the concentration is less than 5 μM, more preferably less than 2 μM or in the range about 0.1-1 μM or about 0.2 μM. Treatment duration may be in the range 1 minute to 12 hours, preferably 10 minutes to 4 hours or more preferably about 0.5, 1, 1.5 or 2 hours.

The centanamycin- or tafuramycin A-treated blood-stage malaria parasites may be used to prepare the immunogenic composition as an isolated, purified or partially purified parasite preparation, or the centanamycin- or tafuramycin A-treated blood-stage malaria parasites may be used to infect red blood cells, which are then used to prepare the immunogenic composition. Alternatively, red blood cells infected with blood-stage malaria parasites may be treated with centanamycin and then used to prepare the immunogenic composition.

In this context, by "isolated" is meant material (e.g. blood-stage malaria parasites) that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material (e.g. blood-stage parasites such as merozoites, schizonts, trophozoites or rings) may be in purified or partially purified form.

As hereinbefore described, one preferred feature of the present invention is that the immunogenic composition comprises a low dose of blood-stage malaria parasites, such as merozoites schizonts, trophozoites or rings.

By "low-dose" in the context of blood-stage malaria parasites (such as merozoites, schizonts, rings or trophozoites, although without limitation thereto) is meant an administered dose wherein the resultant parasite density is sufficiently low that the parasite cannot be detected on a blood smear. In relation to malaria, low dose is typically referred to as a sub-patent infection. A low dose is suitably capable of inducing a T cell response when administered to an animal. Preferably, the immune response is characterised by inducing a T cell response and preferably not inducing B cells to produce detectable levels, or only low levels, of antibodies. A low level of antibody production preferably refers to a level that would not be sufficient to protect an animal against the malaria parasite.

The low dose may be in the form of parasite-infected red blood cells (pRBC). The pRBC may be administered as intact cells or as a lysate. Preferably, the pRBC are in intact form.

The pRBC may be obtained from blood of a parasite-infected animal prior to centanamycin or tafuramycin A treatment. Alternatively, to produce pRBC in vitro, non-infected red blood cells may be obtained from an animal and then infected in vitro with blood-stage malaria parasites pre-treated with centanamycin or tafuramycin A, or with untreated blood-stage malaria parasites so that the pRBC are thereafter treated with centanamycin or tafuramycin A, to thereby achieve low dose pRBC.

A typical low dose is no more than $10^7$ pRBC such as including $10^6$, $10^5$, $10^4$, $10^3$, $10^2$ or 10 pRBC. Preferred low dose ranges include $10^1$-$10^6$, $10^1$-$10^5$, $10^1$-$10^4$, $10^1$-$10^3$, $10^1$-$10^3$, $10^2$-$10^6$ $10^2$-$10^5$, $10^2$-$10^4$, $10^2$-$10^3$, $10^3$-$10^6$, $10^3$-$10^5$, $10^3$-$10^4$, $10^4$-$10^6$ $10^4$-$10^5$ pRBC per dose.

In another embodiment, the low dose may be in the form of purified blood-stage malaria parasites, such as purified merozoites or a mixture of merozoites and schizonts, for example. A low dose is preferably no more than $10^7$ isolated or purified blood-stage malaria parasites, including such as $10^6$, $10^5$, $10^4$, $10^3$, $10^2$ or 10 blood-stage malaria parasites. Preferred low dose ranges include $10^1$-$10^6$, $10^1$-$10^5$, $10^1$-$10^4$, $10^1$-$10^3$, $10^1$-$10^3$, $10^2$-$10^6$ $10^2$-$10^5$, $10^2$-$10^4$, $10^2$-$10^3$, $10^3$-$10^6$, $10^3$-$10^5$, $10^3$-$10^4$, $10^4$-$10^6$ $10^4$-$10^5$ isolated or purified blood-stage parasites per dose.

As used herein, "malaria" includes all forms of the disease caused by protozoan protists of the genus *Plasmodium*.

The genus "*Plasmodium*" includes the species *Plasmodium falciparum, Plasmodium vivax, Plasmodium malariae, Plasmodium ovale, Plasmodium knowlesi, Plasmodium berghei, Plasmodium yoelii, Plasmodium chabaudi* and *Plasmodium vinckei*. In embodiments relevant to malaria in humans, the causative *Plasmodium* species are typically *Plasmodium falciparum* and *Plasmodium vivax*. Suitably, for treatment of humans the immunogenic composition and method of prophylactic or therapeutic treatment of malaria comprises centanamycin- or tafuramycin A-treated merozoites of one or more strains or isolates of *Plasmodium falciparum* and/or *Plasmodium vivax*.

One preferred, unexpected advantage of the present invention is that the centanamyin- or tafuramycin A-treated blood-stage malaria parasites of a particular *Plasmodium* isolate, strain or species will, upon administration to an animal, immunize against infection by heterologous *Plasmodium* isolates, strains and/or species. By "heterologous" pathogens means related pathogens that may be different strains or variants of a same or related species. An example of different strains of a same species is *P. c. chabaudi* AS and *P. c. chabaudi* CB. Heterologous may also refer to related species for example, *P. falciparum* and *P. vivax*.

From the foregoing, it will also be appreciated that another preferred advantage of the present invention is that the immunogenic composition obviates the need for an adjuvant, whether as a component of the immunogenic composition or when administered together with the immunogenic composition. By "adjuvant" is meant an agent which assists, augments or otherwise facilitates the elicitation of an immune response by an immunogen. Non-limiting examples of excluded adjuvants include, Freund's adjuvant, aluminium hydroxide (alum), aluminium phosphate, squalene, IL-12, CpG-oligonucleotide, Montanide ISA720, imiquimod, SBAS2, SBAS4, MF59, MPL, Quil A, QS21 and ISCOMs.

While it is preferred that adjuvant is absent from the immunogenic composition, it will be appreciated that other components such as immunologically acceptable carriers, diluents and/or excipients may be included. Typically, these include solid or liquid fillers, diluents or encapsulating substances that may be safely used in systemic administration. Depending upon the particular route of administration, carriers, diluents and/or excipients may be selected from a group including sugars, starches, cellulose and its derivatives, malt, gelatine, talc, calcium sulfate, vegetable oils, synthetic oils, polyols, alginic acid, isotonic saline, pyrogen-free water, wetting or emulsifying agents, bulking agents, coatings, binders, fillers, disintegrants, lubricants and pH buffering agents (e.g. phosphate buffers) although without limitation thereto. The immunogenic composition and method of prophylactic or therapeutic treatment of malaria may be administered to an animal in any one or more dosage forms that include tablets, dispersions, suspensions, injectable solutions, syrups, troches, capsules, suppositories, aerosols, transdermal patches and the like.

Suitably, the immunogenic composition and method of prevention or treatment of malaria are effective against blood-stage malaria. Blood-stage malaria is a stage where the malaria parasite (e.g. merozoite) enters erythrocytes. In the blood schizont stage, the parasite divides several times to produce new merozoites, which leave the red blood cells and travel within the bloodstream to invade new red blood cells. For the sufferer, blood-stage malaria is typically characterized by successive waves of fever arising from simultaneous waves of merozoites escaping and infecting red blood cells.

The immunogenic composition and method of prevention or treatment of malaria may elicit an immune response that is characterized as a $CD4^+$ T cell-mediated response (including solely $CD4^+$ T cell-mediated responses and mixed $CD4^+$ and $CD8^+$ T cell-mediated responses), typically with little or no antibody response. Preferably, the immunogenic composition and/or method immunize the animal to prevent, inhibit or otherwise protect the animal against subsequent malaria infection. Preferably, a single dose of the immunogenic composition prevents, inhibits or otherwise protects the animal against subsequent malaria infection.

As used herein "animal" refers to any animal capable of infection by a malaria parasite, particularly mammals and preferably humans.

So that preferred embodiments may be described in detail and put into practical effect, reference is made to the following non-limiting Examples.

EXAMPLES

Methods

Passage mice were sacrificed by $CO_2$ inhalation and parasites harvested by cardiac puncture into EDTA collection tubes. Thin blood smears were made to determine parasitaemia.

Blood was diluted to 10 mL in serum free IMDM (Iscoves modified Dulbeccos medium). Blood was always diluted to 10% hematocrit.

Tafuramycin A or centanamycin was diluted from a 2 mM stock (in P.E.T. solution) to 20 µM in medium. Dilution of the 2 mM stock to 20 µM in medium was necessary as the P.E.T solution caused lysis of red blood cells. For 200 nM treatment of red blood cells, 50 µL of the 20 µM solution was added per 5 mL blood. For 2 µM treatment of red blood cells, 500 µL of the 20 µM solution was added per 5 mL blood.

Treated, parasitized red blood cells (pRBC) were washed once with medium and once with PBS before dilution to $5 \times 10^7$, $5 \times 10^6$, $5 \times 10^5$ or $5 \times 10^4$ mL in 0.9% sodium chloride.

5 mice per treatment received 200 µL intravenous immunisations five times one week apart. Final number of treated, pRBC administered per mouse were $10^7$, $10^6$, $10^5$ or $10^4$, as required in each experiment.

Blood smears were made every 2 days and parasitaemia recorded.

Results

Figure 2:
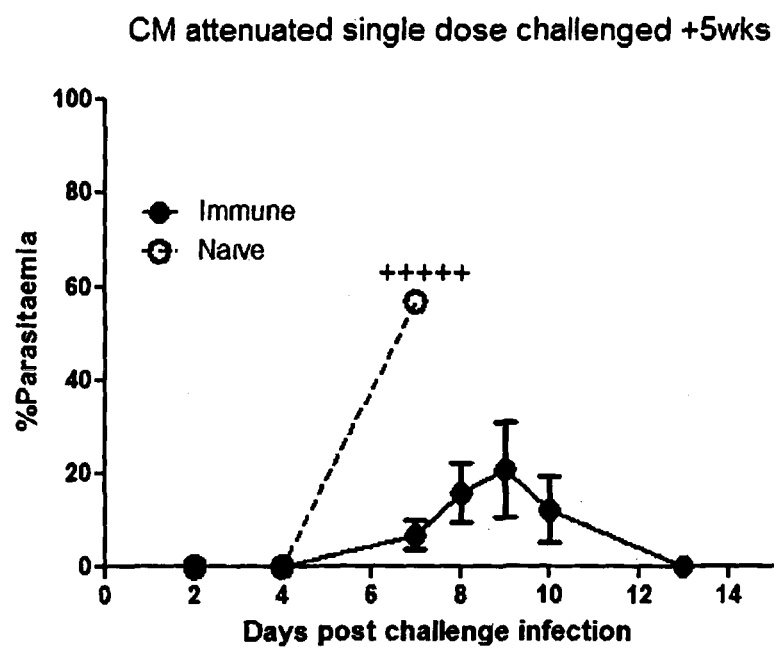
FIG. 2: A/J mice were vaccinated with a single dose of $10^4$ *P. chabaudi* pRBC. Parasites were attenuated in vitro using centanamycin at 2 µM for 40 minutes. pRBC were then washed extensively before being administered to mice. Mice were challenged with *P. chabaudi* ($10^5$ pRBC/mouse—iv) 35 days after the final vaccination. Data represent the mean parasitemia of 5 mice per group +/−SEM. Naïve mice all succumbed or were euthanased by day 8.

The data in FIG. 1 show that exposure of mice to centanamycin attenuated P. chabaudi pRBC induces immunity to virulent challenge. In this study pRBC were treated for 30 min in vitro with 2 µM centanamycin (AS-1-145, compound of formula III) and mice were then given 5 doses of vaccine i.v. (each dose 1 week apart) with each dose containing $10^4$ parasites. Mice were then challenged with $10^5$ homologous WT pRBC and parasitemia followed. This experiment has been repeated several times with similar findings. We have observed that 3 doses of vaccine work effectively and that even a single does of the vaccine induces protection in most animals, as shown in FIG. 2.

Figure 3:
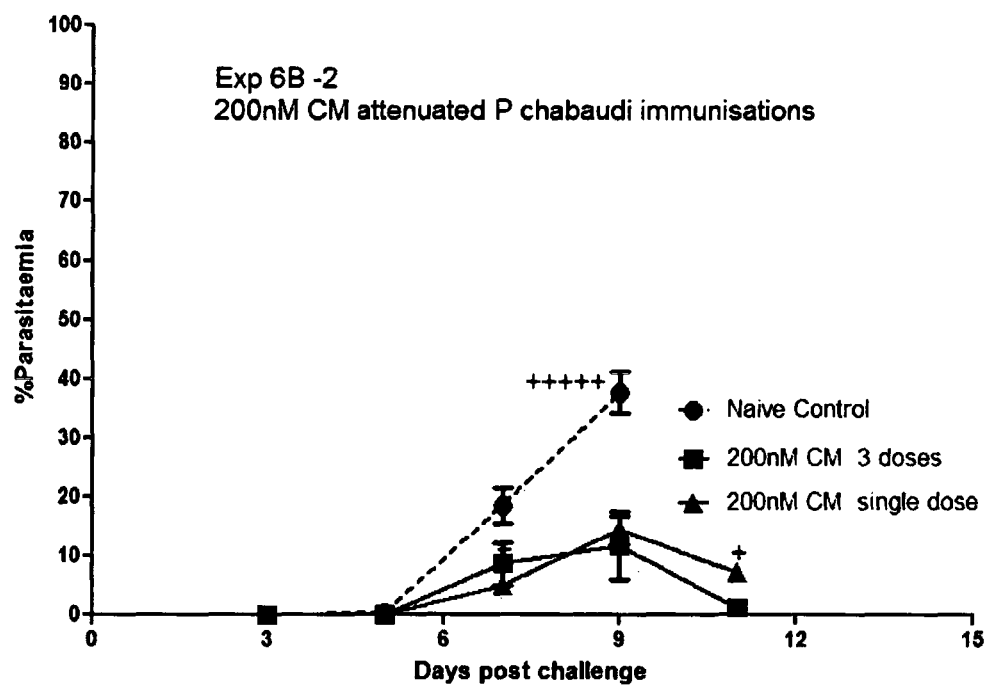
FIG. 3: A/J mice were vaccinated with 3 doses or a single dose of $10^4$ *P. chabaudi* parasitized RBCs. Parasites were attenuated in vitro using centanamycin at 200 nM for 40 minutes. pRBC were then washed extensively before being administered to mice. Mice were challenged with *P. chabaudi* ($10^5$ pRBC/mouse—iv) 21 days after the final vaccination. Data represent the mean parasitemia of 5 mice per group +/−SEM. Naïve mice all succumbed or were euthanased by day 9.

FIG. 3 shows a comparison of mice effectively vaccinated with 3 doses or a single dose of $10^4$ P. chabaudi pRBC that had been treated with 200 nM centanamycin.

Figure 4:
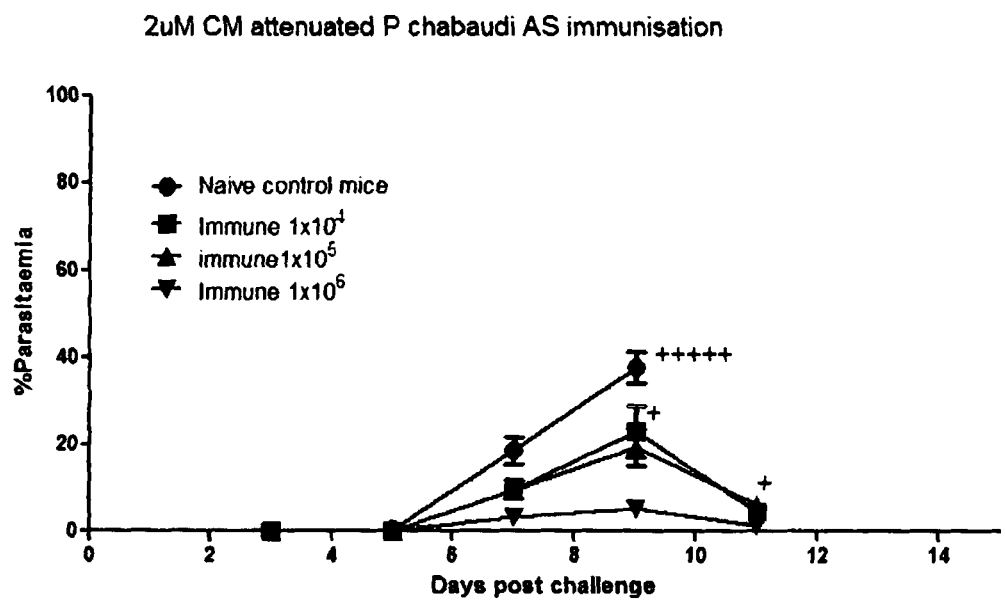
FIG. 4: A/J mice were vaccinated with 3 doses (each dose a week apart) of $10^4$, $10^5$ or $10^6$ *P. chabaudi* pRBC. Parasites were attenuated in vitro using centanamycin at 2 µM for 40 minutes. pRBC were then washed extensively before being administered to mice. Mice were challenged with *P. chabaudi* ($10^5$ pRBC/mouse—iv) 14 days after the final vaccination represent the mean parasitemia of 5 mice per group +/−SEM. Naïve mice all succumbed or were euthanased by day 9.

FIG. 4 shows a comparison of mice vaccinated with 3 doses of $10^4$, $10^5$ or $10^6$ P. chabaudi pRBC. Parasites were attenuated in vitro using centanamycin at 2 µM for 30 minutes. While parasitaemia was lowest for the $10^6$ P. chabaudi immunized mice (e.g. at day 9 post-challenge), each of the $10^4$, $10^5$ and $10^6$ P. chabaudi immunized mice had little or no parasitaemia by day 11 post-challenge.

Figure 5:
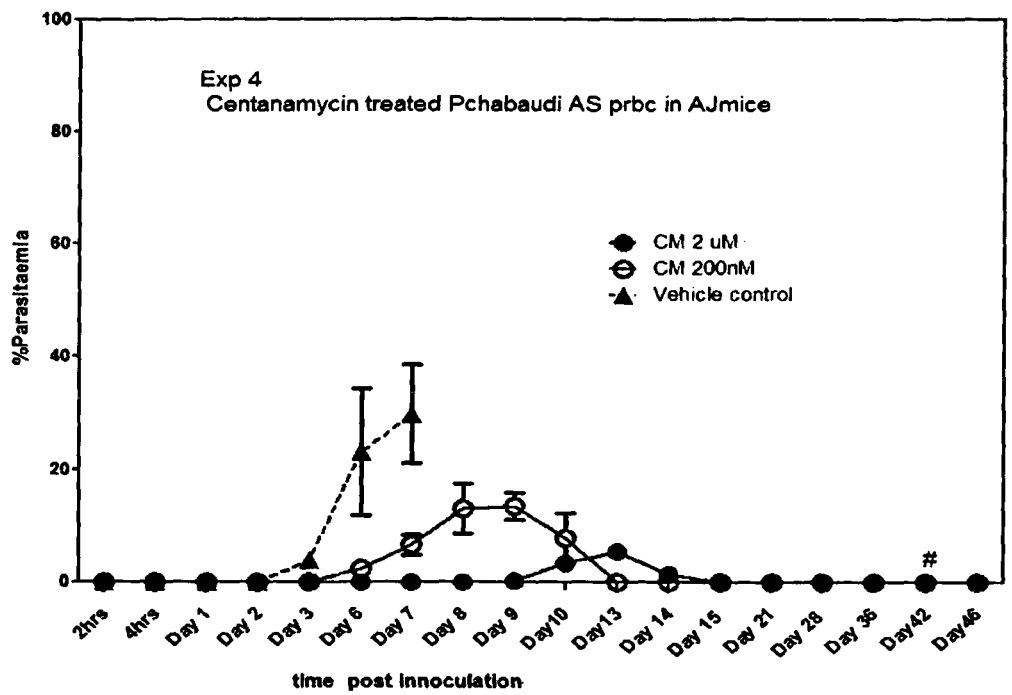
FIG. 5: A/J mice were vaccinated with a single dose of $10^7$ *P. chabaudi* parasitized RBCs. Parasites were attenuated in vitro using centanamycin at 2 µM or 200 nM for 40 minutes. pRBC were then washed extensively before being administered to mice. Mice were challenged with *P. chabaudi* ($10^5$ pRBC/mouse—iv) 14 days after the final vaccination. Data represent the mean parasitemia of 5 mice per group +/−SEM. #500 µL of blood was taken from the immunized mice at day 42 post-innoculation and transferred to naïve reporter mice. There were no parasites detected by microscopy 14 days pre-challenge.

Referring to FIG. 5, mice were vaccinated with a single dose of $10^7$ P. chabaudi pRBC attenuated in vitro using centanamycin at 2 µM or 200 nM for 30 minutes. Mice immunized with $10^7$ P. chabaudi pRBC attenuated using 200 nM centanamycin developed more significant parasitaemia at day 8 and 9 post-challenge than did mice treated with 2 µM centanamycin attenuated parasites. This may have been due to subsequent DNA replication effectively "diluting" the amount of DNA-bound centanamycin per parasite. However, by day 13 post-innoculation mice treated with $10^7$ P. chabaudi pRBC attenuated using 200 nM centanamycin had recovered to the same extent as mice treated with 2 µM centanamycin attenuated parasites.

In this experiment, 500 µL of blood was taken from the immunized mice at day 42 post-innoculation and transferred to naïve reporter mice. There were no parasites detected by microscopy 14 days pre-challenge.

Figure 6:
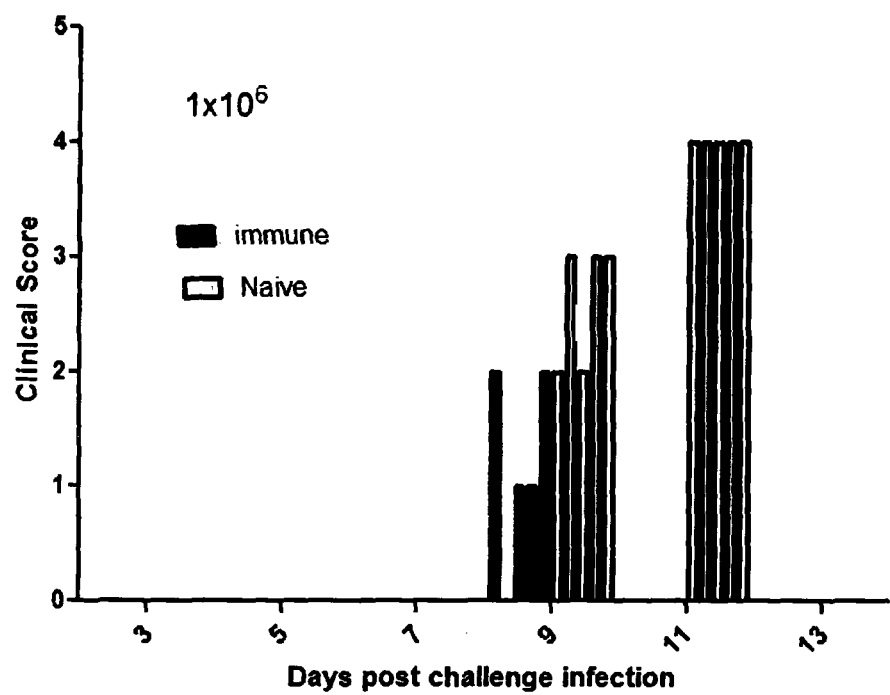
FIG. 6: Clinical Score Data.
Score 0-4 mice displaying two or more Category 2 scores for 2 consecutive days are culled.
Category 1:
Normal (0) Healthy appearance
Mild: (1) Active, responsive, slightly ruffled fur.
(2) Ruffled fur, slow movement, slow responses
Category 2:
Moderate: (3) Ruffled fur, inactive, unresponsive.
Severe: (4) Matted fur, immobile, palour, hematuria high parasite burden.

Referring now to FIG. 6, clinical score data following immunization with $10^6$ centanamycin-treated parasites and challenge show that the mice were protected not only from death and high parasitemia but also from symptoms. This result was surprising in light of a previous report (Hirunpetcharat et al., 1999) showing that while T cells can limit parasite growth they can also cause significant disease and death. It was thought that a by-product of the T cell inflammatory response that was killing parasites was an anti-host response making mice sick. Thus, it is important to note that following vaccination according to the present invention, parasite growth is limited but the mice do not get sick.

We also performed experiments to compare the vaccine prepared using either centanamycin (compound of formula III) or TH-III-149, also known as tafuramycin A (compound of formula II)

AJ mice (5 per group, female) were immunized intravenously with 3 doses of $10^6$ P. chabaudi parasitized red blood cells (pRBC; ring stages) attenuated with either centanamycin or tafuramycin A (compound of formula II). Both compounds were used at a concentration of 2 µM and pRBC were incubated for 40 minutes at 37° C. prior to the compounds being washed from the cells three times. Each immunization was administered 2 weeks apart and mice were then challenged with either $10^5$ P. chabaudi or $10^4$ P. vinckei. pRBC and parasite density in the blood were followed using thin smears stained with Diff Quick. Lower numbers of P. vinckei were used because this parasite is more virulent than P. chabaudi.

Figure 7:
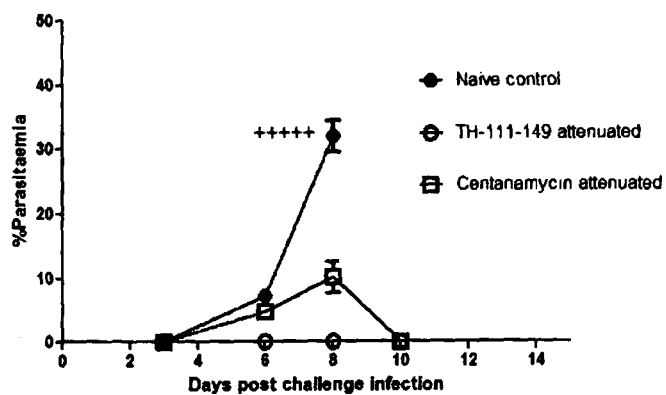
FIG. 7: Comparison of pRBC vaccine prepared using either centanamycin (compound of formula III) or an analog, TH-III-149, also known as tafuramycin A (compound of formula II). Both compounds were used at a concentration of 2 µM and pRBC were incubated for 40 minutes at 37° C. prior to the compounds being washed from the cells three times. A/J mice immunized with either centanamycin or tafuramycin A (TH-III-149) attenuated *P. chabaudi* parasitized red blood cells (pRBC; ring stages) were either subjected to: (A) homologous challenge with $10^5$ *P. chabaudi* parasites; or (B) heterologous challenge with $10^4$ *P. vinckei* parasites.
Figure 7:
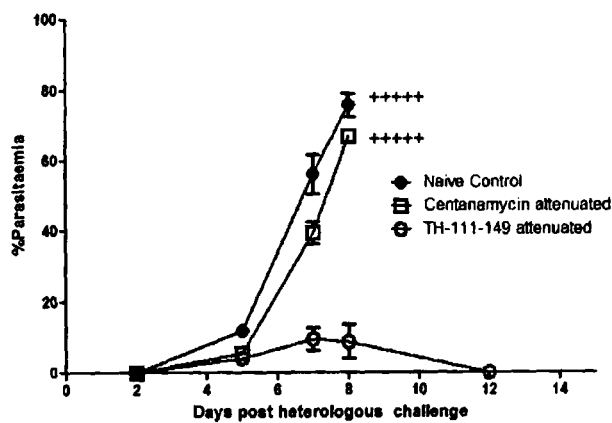

The data in FIGS. 7A and B respectively show the homologous and the heterologous challenge results. The data show near complete protection against homologous challenge and very significant protection against heterologous challenge when the vaccine was produced using tafuramycin A (compound of formula II). Protection against homologous challenge was lower, and against heterologous challenge was even less effective when the vaccine was made using centanamycin for P. vinckei, a particularly virulent species of the parasite. It is worth noting that the data for tafuramycin A the P. vinckei challenge would have been even more impressive except for 1 mouse where the peak parasite density was approximately 20%. But by day 12 all the animals had fully recovered.

The heterologous challenge experiments were also performed with treatment using AS-VIII-104 (compound of formula IV), which performed similarly to centanamycin (not shown).

In further experiments, a comparison of lysed versus intact, treated red blood cells was performed. Mice were immunized with a single intravenous injection of either: (i) $10^6$ P. chabaudi ring stage parasites (in red cells) that were attenuated in vitro by incubation in 2 µM centanamycin for 40 minutes; or (ii) $10^6$ P. chabaudi ring stage parasites (in red cells) that were attenuated in vitro by incubation in 2 µM centanamycin for 40 minutes and then subjected to lysis in distilled water for 2 minutes after which an equal volume of 2×PBS was added to restore the preparation to isotonicity. Mice were challenged 2 weeks after immunization with $10^5$ P. chabaudi pRBC.

Figure 8:
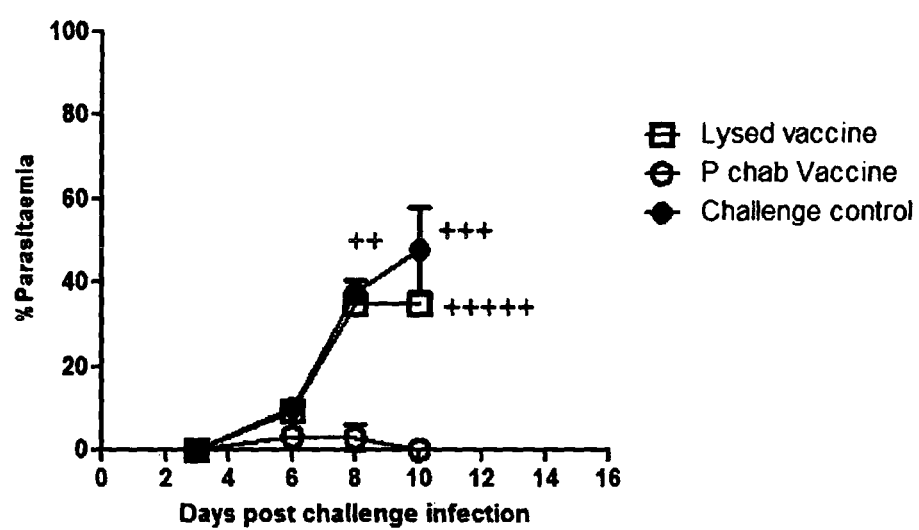
FIG. 8: Requirement for RBC membranes to remain intact for vaccine efficacy. Mice were immunized with a single intravenous injection of either: $10^6$ intact *P. chabaudi* ring stage parasitized red blood cells (pRBC) that were attenuated by incubation in 204 centanamycin (compound of formula III) for 40 minutes; or $10^6$ *P. chabaudi* ring stage pRBC that were attenuated in vitro by incubation in 2 µM centanamycin (compound of formula III) for 40 minutes and then subjected to lysis in distilled water. Mice were challenged 2 weeks after immunization with $10^5$ *P. chabaudi* pRBC.

The results are shown in FIG. 8 and indicate that intact pRBC are a much more effective vaccine than lysed pRBC, showing very low parasitaemia at day 10 compared to lysed pRBC.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

REFERENCES

Ahmed, S. I. et al., Cellular Microbiology, 12: 930-938, 2010
Boger, D. International Publication WO2009/064908
Chavda, S. et al., Bioorganic & Med. Chem. 18:5016-5024, 2010
Elliott, S. R. et al, Infect. Immun. 73:2478, 2005
Hirunpetcharat et al., Parasite. Immunol. 21:319-329, 1999
Howard, T. T. et al., Bioorganic & Med. Chem. 10:2941-2952, 2002
Lee, M. International Publication WO2002/030894
Lee, M. et al. International Publication WO2008/050140
Lee, M. U.S. Pat. No. 6,660,742
McCarthy, J. and Good, M. F. Hum. Vaccine 6:114; 2010
Makobongo, M. et al., Proc. Natl. Acad. Sci. USA 100:2628, 2003
Mamoun, C. B. International Publication 2008/094183
Pinzon-Charry, A. et al., J. Clin. Invest. 120:2967, 2010
Pombo, D. J. et al., Lancet 360:610, 2002
Purcell, L. A. et al., Infect. Immun. 76:1193, 2008a
Purcell, L. A. et al., Vaccine. 26:4880, 2008b
Purnell B, et al., Med. Chem. 2:139, 2006
Sato, A. et al., J. Med. Chem 48:3903, 2005

The invention claimed is:

1. An immunogenic composition comprising blood-stage malaria parasites or red blood cells infected with said blood-stage malaria parasites that have been pre-treated with tafuramycin A or an analog or derivative thereof, prior to administration to a subject, said pre-treatment being effective to attenuate, but not kill said blood stage malaria, and an immunologically acceptable carrier, diluent and/or excipient, wherein tafuramycin A or an analog or derivative thereof is a compound of Formula I:

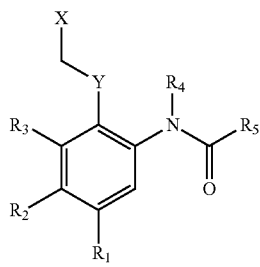

wherein,
$R_1$ is OH;
$R_2$ and $R_3$ form a fused furan ring;
Y is —CH— and forms a five-membered ring with $R_4$;
X is selected from chloro, bromo, iodo, mesylate, tosylate, thio, ammonium, $C_{1-6}$ alkylsulfonyl and $C_{1-6}$ alkylsulfoxyl;
$R_4$ is a —CH$_2$— group bonded to Y to form a five-membered ring; and
$R_5$ is

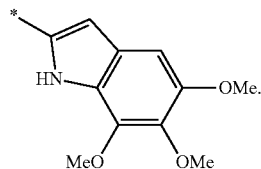 [SMILES: *c1cc2cc(OC)c(OC)c(OC)c2[nH]1]

2. The immunogenic composition of claim 1, which is suitable for administration to a human.

3. The immunogenic composition of claim 1, which does not include an adjuvant.

4. The immunogenic composition of claim 1, which comprises a low dose of blood-stage malaria parasites or red blood cells infected with the blood-stage malaria parasites (pRBC).

5. The immunogenic composition of claim 4, wherein the low dose is selected from the group consisting of: less than $10^6$ blood-stage malaria parasites or treated pRBC; less than $10^5$ blood-stage malaria parasites or pRBC, less than $10^4$ blood-stage malaria parasites or pRBC, and less than $10^2$ blood-stage malaria parasites or pRBC.

6. The immunogenic composition of claim 4, wherein the pRBC are intact.

7. The immunogenic composition of claim 1, wherein the blood-stage malaria parasites comprise merozoites, schizonts, trophozoites and/or rings.

8. The immunogenic composition of claim 7, wherein the blood-stage malaria parasites comprise merozoites.

9. The immunogenic composition of claim 1, wherein administration of a single dose of the immunogenic composition inhibits subsequent malaria infection.

10. The immunogenic composition of claim 1, which elicits a heterologous immune response to infection by one or more other isolates, strains and/or species of Plasmodium.

11. The immunogenic composition of claim 1, wherein tafuramycin A or an analog or derivative thereof is a compound of Formula II:

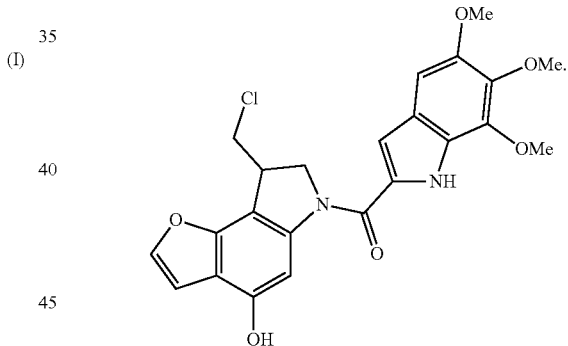

12. The immunogenic composition of claim 1, wherein the concentration of tafuramycin A or analog or derivative thereof is 0.2-2 µM.

13. A method of treating or inhibiting malaria in an animal, said method including the step of administering the immunogenic composition of claim 1 to an animal to thereby inhibit malaria infection or treat an existing malaria infection in said animal.

14. The method of claim 13, wherein administration of a single dose of the immunogenic composition inhibits subsequent malaria infection.

15. The method of claim 14, which provides a heterologous immune response to infection by one or more other isolates, strains and/or species of Plasmodium.

16. The method of claim 13, which excludes the step of administering adjuvant to the animal.

17. The method of claim 13, wherein the animal is a human.

18. The immunogenic composition of claim 1, wherein in formula I:
$R_1$ is OH;
$R_2$ and R3 together form a furan ring; and
X is chloro.

* * * * *